(12) United States Patent
Dhyllon

(10) Patent No.: US 11,464,727 B2
(45) Date of Patent: Oct. 11, 2022

(54) REDUCED-COST COSMETIC FORMULATIONS THAT REDUCE VISIBLE SIGNS OF AGEING

(71) Applicant: Amen Dhyllon, Wynnewood, PA (US)

(72) Inventor: Amen Dhyllon, Wynnewood, PA (US)

(73) Assignee: SERENDIPITY TECHNOLOGIES LLC, Wynnewood, PA (US)

( * ) Notice: Subject to any disclaimer, the term of this patent is extended or adjusted under 35 U.S.C. 154(b) by 0 days.

(21) Appl. No.: 17/035,798

(22) Filed: Sep. 29, 2020

(65) Prior Publication Data

US 2022/0096353 A1   Mar. 31, 2022

(51) Int. Cl.
| | |
|---|---|
| *A61K 8/66* | (2006.01) |
| *A61K 8/34* | (2006.01) |
| *A61K 8/365* | (2006.01) |
| *A61K 8/368* | (2006.01) |
| *A61K 8/41* | (2006.01) |
| *A61K 8/42* | (2006.01) |
| *A61K 8/44* | (2006.01) |
| *A61K 8/46* | (2006.01) |
| *A61K 8/97* | (2017.01) |
| *A61K 8/73* | (2006.01) |
| *A61K 8/92* | (2006.01) |
| *A61Q 19/08* | (2006.01) |
| *A61Q 19/10* | (2006.01) |

(52) U.S. Cl.
CPC .............. *A61K 8/66* (2013.01); *A61K 8/342* (2013.01); *A61K 8/345* (2013.01); *A61K 8/365* (2013.01); *A61K 8/368* (2013.01); *A61K 8/41* (2013.01); *A61K 8/42* (2013.01); *A61K 8/44* (2013.01); *A61K 8/463* (2013.01); *A61K 8/466* (2013.01); *A61K 8/731* (2013.01); *A61K 8/922* (2013.01); *A61K 8/927* (2013.01); *A61K 8/97* (2013.01); *A61Q 19/08* (2013.01); *A61Q 19/10* (2013.01); *A61K 2800/30* (2013.01); *A61K 2800/413* (2013.01); *A61K 2800/43* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 8,283,314 | B1 * | 10/2012 | Marini ................... | A61K 8/355 514/8.1 |
| 2012/0014885 | A1 * | 1/2012 | Collier .................... | A61Q 9/00 424/59 |
| 2014/0309173 | A1 * | 10/2014 | Dreher ............... | A61K 31/4172 548/339.1 |
| 2015/0306011 | A1 * | 10/2015 | Galvez ................... | A61Q 19/08 514/17.2 |

FOREIGN PATENT DOCUMENTS

CN   109330915 A   *   2/2019

OTHER PUBLICATIONS

EPO English translation of CN 109330915A. (Year: 2019).*

* cited by examiner

*Primary Examiner* — Kyung S Chang
(74) *Attorney, Agent, or Firm* — Adam Warwick Bell; Matthew Kaser

(57) ABSTRACT

The present invention discloses a number of formulations (including some that comprise Lunasin and reduce the visible signs of ageing by reducing skin wrinkles) that can be used as body-wash and related skin and hair treatments that can be manufactured using high quality ingredients at a reasonable cost, lower than comparable available products.

12 Claims, No Drawings

REDUCED-COST COSMETIC FORMULATIONS THAT REDUCE VISIBLE SIGNS OF AGEING

FIELD OF THE INVENTION

The embodiments of the present invention relate to a preparation for application to human or animal skin and/or hair for the purpose of improving health and appearance using a range of natural and synthetic ingredients. The present formulations are created with the aim of improving effectiveness and also providing products that have a significantly reduced manufacturing cost. The specific formulations are devised to meet these requirements. The present invention is for external application but may also be used in combination with dietary supplement compositions. The applicant claims a number of compositions which may have various different uses, such that the formulations are encompassed by a generic formulation, with various formulae for use with specific applications being claimed as dependent compositions. The invention provides (1) body wash compositions comprising Argan and Keratin, (2) body wash compositions comprising a cranberry extract, (3) a reduced-cost Argan oil shampoo, and (4) an intensive moisturizing conditioner.

BACKGROUND AND PRIOR ART

Personal care products like body washes, moisturizers and conditioners are popular in the United States and around the world. Body wash compositions should have many or all of the following characteristics: attractive appearance, acceptable scent, good lather, ability to leave the skin feeling soft and smooth, i.e., provide a skin conditioning benefit, be gentle to the skin, be easy to use and rinse off easily. Finally, it is important to provide formulations of very high quality containing natural ingredients, but which can be manufactured at a reasonable cost. The present invention discloses a number of formulations that can be used as body-wash and related skin and hair treatments that can be manufactured using high quality ingredients at a reasonable cost–lower than comparable available products.

Body washes (sometimes also referred to as shower gels) are a general term used to describe liquid surfactant containing formulations used to clean the body. While sometimes considered generically as "soap", such body wash formulations frequently do not contain soaps such as sodium or potassium salts of fatty acids. Conventional body wash formulations, typically contain one of a variety of components including one or more surfactants, various emollients, fragrances and other personal care ingredients. Conventional body washes offer less skin irritation, improved lather in hard water conditions and leave less residues on the skin and bathroom fixtures when compared with common soaps.

Conventional body wash formulations use a surfactant system consisting of a mixture of sodium lauryl ether sulfate (SLES) (an anionic surfactant) and cocamidopropyl betaine (a zwitterionic surfactant). This surfactant mixture is frequently referred to as a SLES/betaine surfactant mixture. While relatively inexpensive and effective, there is pressure from consumers to find a replacement for SLES in personal care compositions. SLES can be a skin irritant for some users. SLES may potentially contain low concentrations of 1,4-dioxane. Dioxane has an LD50 of 5170 mg/kg in rats. This compound is irritating to the eyes and respiratory tract. Exposure may cause damage to the central nervous system, liver and kidneys. Dioxane is classified by the National Toxicology Program as "reasonably anticipated to be a human carcinogen". It is also classified by the IARC as a Group 2B carcinogen: possibly carcinogenic to humans because it is a known carcinogen in other animals.

Thus "sulfate-free" formulations (e.g., body washes) that do not contain sodium lauryl ether sulfate (SLES) are desirable and provided herein. There is also consumer demand for benign surfactants that are derived from bio-renewable sources. Two types of such bio-renewable surfactants include alkyl polyglucosides (APG) which are derivable from glucose and other mono-saccharides and glycine surfactants such as sodium cocoyl glycinate which may be derived from amino acids such as glycine.

The present invention provides a personal care composition which in some embodiments contains no sodium lauryl ether sulfate and no 1,4-dioxane. Various embodiments contain alkyl polyglucosides (APG) derived from glucose and sodium cocoyl glycinate.

The present invention discloses a number of formulations that can be used as body-wash and related skin and hair treatments that can be manufactured using high quality ingredients at a reasonable cost lower than comparable available products. The present formulations improve the general condition of the skin without irritation and without leaving a surfactant/soap residue.

The invention will now be illustrated by the following Examples. Percentages are by weight.

SUMMARY OF THE INVENTION

The invention provides a skin-cleaning and nourishing formulation with reduced manufacturing cost, high effectiveness, easy formulation and improved performance.

The present formulations improve the general condition of the skin without irritation and without leaving a surfactant/soap residue.

Some of the embodiments of the invention comprise LUNASIN and reduce the visible signs of ageing by reducing skin wrinkles.

Under controlled studies the compositions comprising LUNASIN have been found to reduce visible signs of ageing. See U.S. Provisional application No. 60/999,053 filed 12 Oct. 2007 entitled "Lunasin-induced regulation of disease-related gene expression"; 60/594,487 "Gene Expression Profiles In Normal And Tumorigenic Cells"; 60/261,217 "The Use of Lunasin Peptide as a Transcriptional Activator to Prevent Cancer and Related Methods for Treatment, Monitoring and Prognosis"; and PCT/US05/04868 "The Use of Lunasin Peptide as a Transcriptional Activator to Prevent Cancer and Related Methods for Treatment, Monitoring and Prognosis" all of which are incorporated by reference.

Lunasin, a well-known peptide present in the soybean, has displayed a positive impact on numerous physiological functions. Notably, Lunasin suppresses reduction of type II collagen, the basis for articular cartilage. Lunasin is found in soybeans, barley, rye, and wheat (see U.S. Pat. No. 7,829,277 incorporated by reference). Lunasin exerts its hypocholesterolemic activity by blocking acetylation of histone H3 Lys14 residue thereby reducing the production of HMG-CoA reductase with concomitant decrease in cholesterol biosynthesis. Lunasin also increases cellular production of LDL receptors leading to removal of plasma LDL cholesterol. Lunasin is a 43 amino acid small subunit of a soybean 2S albumin. The polynucleotide encoding the lunasin peptide, and the peptide sequence of lunasin are known and disclosed in U.S. Pat. No. 6,544,956 (hereby incorporated by reference in its entirety) in which the lunasin peptide is encoded by bases 80-208 of SEQ ID NO:1, and the peptide is defined by residues 22-64 of SEQ ID NO:2. The carboxyl end of lunasin contains a chromatin-binding domain, a cell adhesion motif Arg-Gly-Asp (RGD) followed by eight Asp residues. The chromatin-binding domain consists of a 10-amino acid helical region homologous to a short conserved region found in other chromatin binding proteins. Mammalian studies provide evidence that lunasin may play a role in the cell cycle control. Exogenous addition of chemically synthesized lunasin to mammalian cells demonstrates that lunasin colocalizes with hypoacetylated chromatin; preferentially binds deacetylated histone H4 in vitro; and prevents histone H3 and H4 acetylation in vivo in the presence of a histone deacetylase inhibitor. Acetylation and deacetylation of conserved histone N-terminal tails result in chromatin conformational changes that induce or suppress gene expression. It has been hypothesized that Lunasin modulates changes in chromatin organization by modifying histone tails, thereby, affecting gene expression that leads to its anti-neoplastic properties. Importantly, Lunasin suppresses the increase in MMP-3 and MMP-13 caused by IL-1β and inhibits decrease in TIMP-1 and TIMP-2 expressions caused by IL-1β. Lunasin suppresses reduction of type II collagen, the basis for articular cartilage. Lunasin also attenuates activation of the JAK2/STAT1/IRF-1 pathway.

When combined with the formulations of the present invention, Lunasin will reduce visible signs of ageing by reducing wrinkles by suppresses reduction of type II collagen. These and other features, aspects, and advantages of the present invention will become better understood from a reading of the following description, and appended claims.

DETAILED DESCRIPTION

The present invention provides personal care compositions which comprise at least one surfactant and use high quality, mostly natural ingredients at a reasonable cost, lower than comparable available products.

We herein disclose skin-cleaning and nourishing formulations with reduced manufacturing cost, high effectiveness, easy formulation and improved performance. These formulations improve the general condition of the skin without irritation, and importantly, without leaving a surfactant/soap residue. Some of the embodiments of the invention comprise Lunasin and reduce the visible signs of ageing by reducing skin wrinkles. Under controlled studies the compositions comprising Lunasin have been found to reduce visible signs of ageing.

A very important advantage is that that the price of the finished product is less than that of conventional formulations.

One object of the present invention is to provide effective and reliable body-wash, and improve the general condition of the skin without irritation and without leaving a surfactant/soap residue. The formulation of the invention is cheaper to create than that of the conventional commercial formulations, yet it provides improved quality.

Formulation 1

This formulation is generally used as a body-wash or body-scrub, but can also be used as a shampoo. Formulation 1 comprises (or in some embodiments, consists of) the following, with all percentages shown as weight-percent (wt %):

Water, 61% (optionally from 40% to 80%)
A rheology modifier such as Aculyn-60, 0.700% (optionally from 0.3% to 1.4%)
C14-16 alpha olefin sulfonate (AOS), 2.0% (optionally from 1% to 4%)
Cocamide MEA or DEA, 1.0% (optionally from 0.5% to 2%)
Decyl Glucoside (a mild non-ionic surfactant), 8.0% (optionally from 4% to 16%)
Sodium Benzoate, 0.2% (optionally from 0.1% to 0.4%)
Potassium Sorbate, 0.2% (optionally from 0.1% to 0.4%)
EDTA, 0.100% (optionally from 0% to 0.2%)
Imidazolidinyl urea, 0.3% (optionally from 0% to 0.6%) as a preservative
Niacinamide or any other B vitamin, 0.2% (optionally from 0.01% to 1%)
Allantoin, 0.2% (optionally from 0.1% to 0.4%)
Glycerine, 1.0% (optionally from 0.5% to 2%)
Polyquaternium-10 (PQ-10), 0.2% (optionally from 0.1% to 0.4%)

Preferred embodiments of Formulation 1 use Decyl Glucoside as the surfactant (from 0.5% to 10% wt %). Sodium lauryl ether sulfate (SLES) (an anionic surfactant) and cocamidopropyl betaine are specifically excluded from some embodiments, such as Formulation 1, as these components have been shown to cause irritation to sensitive skin.

Formulation 2

This formulation comprises (or optionally consists of) the ingredients of Formulation 1, and also includes Lunasin, a polypeptide is proven to reduce visible signs of ageing and displays a positive impact on numerous physiological functions. Notably, Lunasin suppresses reduction of type II collagen, the basis for articular cartilage.

Formulation 3

This formulation comprises (or optionally consists of) the ingredients of Formulation 1, but Sodium Cocoyl Isethionate is used as the surfactant, 4.0% (optionally from 0.5% to 8%).

Formulation 4

This formulation comprises (or optionally consists of) the ingredients of Formulation 1, but also includes:
Sodium Lactate, 0.2% (optionally from 0.5% to 2%)
Aloe Vera Extract, 0.3% (optionally from 0.1% to 0.6%)
An antiseptic such as Citrimide, 0.3% (optionally from 0.1% to 0.6%)

Formulation 5

This formulation comprises the ingredients of Formulation 1, 2, 3 or 4, additionally including alkyl polyglucoside as a surfactant.

Formulation 6

This formulation comprises (or optionally consists of) the ingredients of Formulation 1, 2, 3, 4 or 5 and also comprises: Sodium lauryl ether sulfate (SLES), from 0.10% to 1.0%.

Formulation 7

This formulation comprises the composition of formulation 1, 2, 3, 4, 5 or 6, additionally including: Cocamidopropyl betaine (CAPB), 8.0% (optionally from 4% to 16%).

Any of the above formulations may additionally/optionally include coloring agents, fragrances agents and/or oils.

Any of the above formulations may additionally/optionally include hydrocarbon oils or waxes, silicones, pearlising agents, preservatives, perfumes and colourants.

Any of the above formulations may additionally/optionally include rheology modifiers. Formulations are generally water-based and include amphipathic components.

Formulations may additionally/optionally include GHK-Cu (a Copper peptide GHK-Cu is a naturally occurring copper complex of the tripeptide glycyl-L-histidyl-L-lysine) that can have a firming effect on skin when topically applied.

Formulations may additionally/optionally include Palmitoyl Pentapeptide that is believed to increase collagen synthesis.

Formulations may additionally/optionally include Pentapeptide 3, which is believed to relax muscles in the skin, therefore reducing wrinkles.

Formulations may additionally/optionally include and rice & soy peptides, such as Lunasin.

Alternative formulations may additionally/optionally include at least one alkyl polyglucoside as a surfactant, unless explicitly excluded. This is a water-soluble cellulose ether base material substituted with a hydrophobic group having a carbon chain with 8 to 15 carbon atoms; wherein the water-soluble cellulose ether base material has a weight average molecular weight, Mw, of >800,000 Daltons; and wherein the personal care composition contains <0.01 wt % alkyl sulfate and <0.01 wt % alkyl ether sulfate.

Some formulations may optionally include a combination of several or all of the following ingredients: Cetyl Alcohol, Olivem, Bee's Wax, CCTG (Capric TriGlyceride), Cetrimide, HEC (hydroxy-ethylcellulose), Glycerin, Kara base, T-20 (a surfactant), PG (Propylene glycol), EDTA, Sodium Benzoate, Phenoxy, Coconut Oil, Argon Oil, Jojoba Oil, Curry leaf Extract, Beetroot Extract. Diasleek-802, Karacyne, DC-245 (a Silicone fluid), Soya Lecithin, Collagen, Biotin, Cetrimonium Chloride, Fragrance Coconut Milk, D Penthanol, G-700 (a Sunscreen), Vitamin E, Vitamin B-3, Amaport and CAPB.

Other ingredients and additives may include, for example, cosmetic conditioning oils, cetyl ethylhexanoate, oil thickeners such as dextrin palmitate, and additional components selected from the group consisting of oleyl erucate, hydrogenated polyisobutene, PPG-3 caprylyl ether, vitamin E, panthenol, panthenyl ethyl ether, plant extracts, vitamins and nutrients.

The formulations of the invention may be formulated in a number of ways using a number of non-active ingredients, carriers, fillers and fragrances and consistency enhancers. The composition of the present invention may include other additional components, which may be selected according to the desired characteristics of the final composition and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include oils such as oleyl erucate with a trade name of Cetiol J 600 available from Cognis, part of BASF, hydrogenated polyisobutene with a trade name of ParLeam available from NOF, PPG-3 caprylyl ether with a trade name of Sofcare GP-1 from Kao Chemical; scalp care ingredients such as vitamin E with tradename Emix-d available from Eisai, panthenol available from Roche, panthenyl ethyl ether available from Roche, plant extracts, and nutrients.

The above formulations are for use as body-washes, but optional shampoo formulations may be created by using increased amounts of foaming agents. The most common foaming agents used in personal care are chemicals sodium laureth sulfate (SLES), sodium lauryl sulfate (aka sodium dodecyl sulfate or SLS) and coco-glucoside. Foaming beauty products generally contain SLES at about 67.3%, coco-glucoside at about 16.5% and SLS at about 12.3%.

Gold Nanoparticles

The formulations of the invention, in some embodiments, may include metal nanoparticles, for example gold nanoparticles. Generally either gold nanospheres or goldnanotubes may be used. The invention further uses a synthetic metal nanotube, the synthetic nanotube being substantially hollow and having dimensions of between about 20 nm and about 100 nm in mean diameter and at least between about 0.1 μm and 4 μm in mean length. In a more preferred embodiment the mean diameter is between about 30 nm and 80 nm. In a more preferred embodiment the mean length is between about 4 μm and about 50 μm, for example, about 6 μm, about 8 μm, about 10 μm, about 15 μm, about 20 μm, about 25 μm, about 30 μm, about 40 μm, and about 50 μm, and any other length therebetween. In one embodiment the synthetic nanotube has a wall of mean dimension of between about 2.4 mm and about 7.3 nm across. In a preferred embodiment the wall has a mean dimension of about 5 mm. In one preferred embodiment the synthetic nanotube comprises a metal selected from the group consisting of gold, silver, platinum, copper, aluminum, palladium, cadmium, iridium, rhodium, and the like. See U.S. Pat. No. 8,137,759, US20170184505, and U.S. Pat. No. 9,297,801, and Holt, J. K. et al., Science 312, 1034-1037 (2006); Hinds, B. J. et al., Science 303, 62-65 (2004); Zhang, M. et al. Science 309, 1215-1219 (2005); and Huang, Y. et al., Science 294, 1313-1317 (2001), all incorporated by reference herein. Gold nanotubes in particular may be used in the formulations of the invention. Their shape and size is entirely dependent on the template on which they are made. Various cosmetics companies such as L'Oreal, Dior and Olay have used nanoparticles, but none, to the knowledge of the applicant, has used gold nanotubes. Over time, the collagen in skin becomes degraded and contributes to the signs of aging (i.e. wrinkles). One process known to age skin is the formation of advanced glycation end products (AGEs) which are the products of reactions between carbohydrates and collagen. The accumulation of AGE in the skin causes the skin to lose some of its elasticity. Gold nanotubes compete with carbohydrates and bind amino acids like lysine and arginine, thereby inhibiting AEG formation. The applicant believes that incorporation of gold nanotubes will inhibit formation of advanced glycation end products and therefore reduce skin ageing. As used in the present invention, nanoparticles may be at a concentration above zero, but less than 0.00001 wt %, or less than 0.0001 wt %, or less than 0.001 wt %, preferably, less than 0.01 wt %.

Telomerase Activators

The formulations of the invention, in some embodiments, may include telomerase activators, for example those engineered by Geron Corporation, such as the natural product-derived telomerase activator (TA-65®) which activates keratinocytes, fibroblasts, and immune cells in culture See Rejuvenation Res. 2011 February; 14(1): 45-56, incorporated by reference. The formulation may include 10-50 mg/ml for topical application. Telomerase is the enzyme responsible for the maintenance of telomeres, essential structures that cap and protect the ends of linear chromosomes. Human telomeres are made of tandem copies of $(TTAGGG)_n$ DNA repeats and of associated proteins, which together form a protective capping complex. This cap protects chromosomal ends from degradation, interchromosomal fusions and from being recognized as double-stranded (ds) DNA breaks, a form of DNA damage. Because of problems associated with the replication of the ends of linear DNA molecules, the so-called end-replication problems, telomeres shorten each time human somatic cells divide and this attrition limits their lifespan. Once the shortest telomere become uncapped, a DNA damage response is induced that mobilizes the p53 and p16/pRB pathways, which then act together to induce senescence, a viable state of irreversible quiescence. If the p53 and p16/pRB pathways are disabled, the cells will ignore these growth inhibitory signals and will continue to divide and shorten their telomeres. Eventually, terminal telomere shortening lead to crisis, a non-viable state associated with programmed cell death. Crisis is triggered by recurrent cycles of telomere-telomere fusions, anaphase bridges and chromosome breakage. When present, telomerase can prevent the induction of senescence and crisis and extend cellular lifespan by the synthesis and addition of new telomeric repeats to the telomeres. The formulations of the invention may include telomerase activators such as TA-65 at a concentration of 0.001-100 mg/ml, or 0.001-50 mg/ml, or 0.001-1 mg/ml, for example in a preferred embodiment 1-10 mg/ml for topical application. Sometimes the concentration may be less than 0.01 mg/ml. As used in the present invention, the telomerase activator may be at a concentration above zero, but less than 0.01 mg/ml, or less than 0.001 mg/ml, or less than 0.0001 mg/ml. Any other telomerase activator may be likewise used.

Colloidal Silver

The formulations of the invention, in some embodiments, may include colloidal silver which is believed can reduce the signs of skin ageing. It may decrease the irritating effects caused by oxidative stress and stimulates skin elasticity. However it should be used in very small quantities because silver can cause generalized argyria, which is usually a permanent slate-gray to blue discoloration of the skin predominantly on sun-exposed areas. Very rarely, excessive colloidal silver ingestion can cause more serious health problems such as seizures and kidney damage. Thus, if used in the present invention, colloidal silver is used at a concentration of less than 0.01 wt %. As used in the present invention, colloidal silver may be at a concentration above zero, but less than 0.00001 wt %, or less than 0.0001 wt %, or less than 0.001 wt %, preferably, less than 0.01 wt %.

Methods of Preparation

The elements may be combined at room temperature and mixed and homogenized using a conventional stirrer or mixer. In other embodiments, the elements may be combined at an elevated temperature. Components are added with agitation. The mixture is then slowly cooled to room temperature. The mixtures obtained can be then added into hair care or skin care products such as shampoos and body soaps. The mixtures can be added directly or as a pre-emulsified emulsion using anionic, nonionic, or cationic surfactants as an emulsifier.

In various embodiments that require Lunasin, the Lunasin is extracted from soy beans using cold pressing, and never exposed to a temperature above 25 Centigrade.

EXAMPLES

The embodiments described herein are given as examples. In some examples, we provide a list of the ingredients with no set quantities. However, it will be clear that any quantities provided will be those that are practical and consistent with customary human consumption. Another example is the ranges of the quantities of the ingredients with a 20% +/±variation, i.e., with a variance of 20% more or less of each ingredient. In other embodiments, the variation may be plus or minus 5%, 10%, 15%, 25%, 30%, 35%, 40%, 50%, 60% or 75% by weight. Indeed, in certain embodiments, the amount of any particular ingredient may be several times that shown, for example twice, three times, 5 times or ten times that shown in the examples. A further example is the optimum quantities of the ingredients. Other non-enumerated ingredients may also be present. Note that in alternative embodiments the invention may encompass a formulation consisting essentially of a combination of any of the listed active components, but not including any other active components. These formulations may include non-active ingredients such as fillers and carriers, scent enhancers, perfumes, pearlizing agents, etc.

The below examples show different specific formulations.

Body Wash Formulations (reduced cost formulation)

| No. | Ingredient | Wt % | Price/Kg | Total |
|---|---|---|---|---|
| 1 | Water to make | 61.620% | 4.000 | 2.4648 |
| 2 | Aculyn -60 | 0.700% | 1100.000 | 7.7000 |
| 3 | SCI | 4.000% | 380.000 | 15.2000 |
| 4 | AOS (P) | 2.000% | 210.000 | 4.2000 |
| 5 | CMEA | 1.000% | 300.000 | 3.0000 |
| 6 | Decyl Glucoside | 8.000% | 300.000 | 24.0000 |
| 7 | CAPB | 8.000% | 100.000 | 8.0000 |
| 8 | CDEA | 2.000% | 170.000 | 3.4000 |
| 9 | CADA | 2.000% | 285.000 | 5.7000 |
| 10 | Gantle Care | 2.000% | 350.000 | 7.0000 |
| 11 | Sodium Benzoate | 0.200% | 140.000 | 0.2800 |
| 12 | Potassium Sorbate | 0.200% | 730.000 | 1.4600 |
| 13 | EDTA | 0.100% | 110.000 | 0.1100 |
| 14 | Imidazole Urea | 0.300% | 1370.000 | 4.1100 |
| 15 | ESS | 5.000% | 300.000 | 15.0000 |
| 16 | Niacatinamide | 0.200% | 1400.000 | 2.8000 |
| 17 | Allantoin | 0.200% | 420.000 | 0.8400 |
| 18 | Glycerin | 1.000% | 100.000 | 1.0000 |
| 19 | PQ-10 | 0.200% | 200.000 | 0.4000 |
| 20 | Sodium Lactate | 0.200% | 150.000 | 0.3000 |
| 21 | Aloe Vera Extract | 0.300% | 420.000 | 1.2600 |
| 22 | Cetrimide | 0.300% | 1000.000 | 3.0000 |
| 23 | Color | 0.010% | 1000.000 | 0.1000 |
| 24 | Fragrance | 0.700% | 1500.000 | 10.5000 |
| 26 | Oil | 0.020% | 1900.000 | 0.3800 |
| 27 | SLS | 0.400% | 300.000 | 1.2000 |
| | Total | 100.7% | 14739 | 123.5048 |

Argan Oil Keratin Mask (reduced cost formulation)

| No. | Ingredient | Wt % | Price/Kg | Total |
|---|---|---|---|---|
| 1 | Water to make | 70.700% | 4.000 | 2.8280 |
| 2 | Cetyl Alcohol | 5.000% | 125.000 | 6.2500 |
| 3 | Olivem - 1000 | 2.000% | 1200.000 | 24.0000 |
| 4 | Bees' Wax | 0.400% | 265.000 | 1.0600 |
| 5 | CCTG | 2.500% | 475.000 | 11.8750 |
| 6 | Cetrimide | 1.000% | 900.000 | 9.0000 |
| 7 | HEC | 0.300% | 1160.000 | 3.4800 |
| 8 | Glycerin | 1.500% | 100.000 | 1.5000 |
| 9 | Kara base | 4.000% | 1300.000 | 52.0000 |
| 10 | T-20 | 0.750% | 230.000 | 1.7250 |
| 11 | PG | 0.500% | 156.000 | 0.7800 |
| 12 | EDTA | 0.100% | 240.000 | 0.2400 |
| 13 | Sodium Benzoate | 0.200% | 130.000 | 0.2600 |
| 14 | Phenoxy | 0.200% | 245.000 | 0.4900 |
| 15 | Coconut Oil | 1.500% | 380.000 | 5.7000 |
| 16 | Argon Oil | 0.100% | 2800.000 | 2.8000 |
| 17 | Jojoba Oil | 0.100% | 1000.000 | 1.0000 |
| 18 | Curry leaf Extract | 0.300% | 780.000 | 2.3400 |
| 19 | Beetroot Extract | 0.200% | 850.000 | 1.7000 |
| 20 | Diasleek -802 | 0.800% | 1750.000 | 14.0000 |
| 22 | Cyclopentasiloxane (DC-245) | 0.750% | 520.000 | 3.9000 |
| 24 | Collagen CLR | 0.100% | 8000.000 | 8.0000 |
| 27 | Fragrance Coconut Milk | 0.300% | 1700.000 | 5.1000 |
| 28 | D Penthanol | 0.200% | 2800.000 | 5.6000 |
| 29 | G-700 | 0.500% | 80.000 | 0.4000 |
| 33 | CAPB | 6.000% | 78.000 | 4.6800 |
| | Total | 100.000% | 27110.000 | 170.7080 |

| Argan Oil Shampoo (reduced cost formulation) |||||
|---|---|---|---|---|
| No. | Ingredient | Wt % | Price/Kg | Total |
| 1 | Water to make | 63.340% | 5.000 | 3.1670 |
| 2 | Aculyn -60 | 0.400% | 1100.000 | 4.4000 |
| 3 | SCI | 1.000% | 380.000 | 3.8000 |
| 4 | G-100 (CMEA) | 1.000% | 210.000 | 2.1000 |
| 5 | PQ - 10 | 0.300% | 3100.000 | 9.3000 |
| 6 | Carrier/filler | 19.000% | 300.000 | 57.0000 |
| 7 | CAPB | 3.000% | 100.000 | 3.0000 |
| 8 | AOS (P) | 1.200% | 170.000 | 2.0400 |
| 9 | EDTA | 0.100% | 285.000 | 0.2850 |
| 10 | Sodium Benzoate | 0.200% | 350.000 | 0.7000 |
| 11 | Potassium Sorbate | 0.200% | 850.000 | 1.7000 |
| 12 | Imidazole Urea | 0.100% | 450.000 | 0.4500 |
| 13 | Glycerin | 1.500% | 110.000 | 1.6500 |
| 14 | Diaslik 802 | 1.200% | 1370.000 | 16.4400 |
| 15 | D - Penthanol | 0.100% | 8300.000 | 8.3000 |
| 16 | Dc-193 | 0.100% | 1650.000 | 1.6500 |
| 17 | Aloe Vera Extract | 0.300% | 420.000 | 1.2600 |
| 18 | CADA | 3.000% | 340.000 | 10.2000 |
| 19 | Decyl Glucoside | 0.000% | 200.000 | 0.0000 |
| 20 | Ginseng Extract | 0.400% | 1500.000 | 6.0000 |
| 21 | Nori Complex | 0.100% | 6000.000 | 6.0000 |
| 22 | Argan Oil | 0.100% | 3000.000 | 3.0000 |
| 23 | Biotin | 0.010% | 85000.000 | 8.5000 |
| 24 | ACV | 1.000% | 300.000 | 3.0000 |
| 25 | Curry Leaf Extract | 0.200% | 900.000 | 1.8000 |
| 26 | Green Tea Champian Gogia | 0.400% | 1900.000 | 7.6000 |
| 27 | Color Yellow (Bush) | 0.020% | 500.000 | 0.1000 |
| 28 | Color Orange (Bush) | 0.020% | 500.000 | 0.1000 |
| | Total | 98.290% | 119290.000 | 163.5420 |

Components of Formulations and Definitions

The above components may be present as variants or salts thereof or may be compounded with various other components such as carriers, fillers, oils, emulsifiers. They may be present in solid, powder or liquid form. While the embodiments of the present invention have been illustrated and described in the examples, the invention is not meant to be limited by the examples and the meets and bounds of some of the embodiments of the invention is set out in the claims.

Terms and Definitions

The following are general definitions of various components that may be used in the formulations of the inventions. All of the following components may be compounded into one or more formulations, but are not intended to represent an exclusive list of ingredients. While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of". All percentages, parts and ratios are based upon the total weight of the compositions of the present invention, unless otherwise specified. All such weights as they pertain to listed ingredients are based on the active level and, therefore, do not include carriers or by-products that may be included in commercially available materials. Herein, "mixture" is meant to include a simple

| Intensive Moisturizing Hair Conditioner (reduced cost formulation) |||||
|---|---|---|---|---|
| No. | Ingredient | Wt % | Price/Kg | Total |
| 1 | Water to make | 71.250% | 3.000 | 2.1375 |
| 2 | Cetyl Alcohol | 5.000% | 125.000 | 6.2500 |
| 3 | Olivem - 1000 | 1.000% | 1730.000 | 17.3000 |
| 4 | Bees' Wax | 0.400% | 265.000 | 1.0600 |
| 5 | CCTG | 2.500% | 475.000 | 11.8750 |
| 6 | Cetrimide | 1.000% | 900.000 | 9.0000 |
| 7 | HEC | 0.300% | 1160.000 | 3.4800 |
| 8 | Glycerin | 1.500% | 120.000 | 1.8000 |
| 9 | Kara base | 2.000% | 1300.000 | 26.0000 |
| 10 | T-20 | 0.750% | 230.000 | 1.7250 |
| 11 | PG | 0.500% | 156.000 | 0.7800 |
| 12 | EDTA | 0.100% | 240.000 | 0.2400 |
| 13 | Sodium Benzoate | 0.200% | 130.000 | 0.2600 |
| 14 | Phenoxy | 0.200% | 245.000 | 0.4900 |
| 15 | Coconut Oil | 1.500% | 380.000 | 5.7000 |
| 16 | Argon Oil | 0.200% | 2800.000 | 5.6000 |
| 17 | Jojoba Oil | 0.200% | 1000.000 | 2.0000 |
| 18 | Curry leaf Extract | 0.300% | 780.000 | 2.3400 |
| 19 | Beetroot Extract | 0.200% | 850.000 | 1.7000 |
| 20 | Diasleek -802 | 1.200% | 1750.000 | 21.0000 |
| 21 | Karacyne | 0.200% | 10000.000 | 20.0000 |
| 22 | DC-245 | 0.750% | 520.000 | 3.9000 |
| 23 | Soya Lecithin | 0.200% | 1850.000 | 3.7000 |
| 24 | Collagen CLR | 0.200% | 8000.000 | 16.0000 |
| 25 | Biotin | 0.050% | 23000.000 | 11.5000 |
| 26 | Cetrimonium Chloride | 0.500% | 230.000 | 1.1500 |
| 27 | Fragrance Sweet Lavender | 0.400% | 1700.000 | 6.8000 |
| 28 | D Penthanol | 0.200% | 5600.000 | 11.2000 |
| 29 | G-700 | 0.500% | 80.000 | 0.4000 |
| 30 | Vitamin E | 0.100% | 900.000 | 0.9000 |
| 31 | Vitamin B-3 | 0.100% | 800.000 | 0.8000 |
| 32 | Amaport | 0.100% | 6000.000 | 6.0000 |
| 33 | CAPB | 6.000% | 78.000 | 4.6800 |
| | Total | 99.600% | 65539.000 | 207.7675 | combination of materials and any compounds that may result from their combination.

Water=H₂O which may include de-minimums amounts of salts, carbonates, metals or other typical components. Water: Although water is described in the tables as "Balance to make 100%" or as a given percentage, it must be understood that the percentages in the formulations do not always add up to 100% and that in various formulations additional non-listed ingredients may be added and used. Thus, the amount of water may be added as needed, and may not provide the entire balance of any particular formulation. For example, water may be present in amounts from 1% to 95%, from 5% to 90% or from 5% to 75% or any other percentage.

Cetyl Alcohol=Cetyl alcohol, also known as hexadecan-1-ol and palmityl alcohol, is a fatty alcohol with the formula CH315OH. At room temperature, cetyl alcohol takes the form of a waxy white solid or flakes. The name cetyl derives from the whale oil from which it was first isolated.

OLIVEM®=a white to ivory waxy flake solid. It is a PEG-free co-emulsifier, self-emulsifying multifunctional ingredient, HLB 8-9, that is COSMOS-validated Bee's Wax=Beeswax (cera alba) is a natural wax produced by honey bees of the genus *Apis*. The wax is formed into "scales" by eight wax-producing glands of bees.

CCTG=Capric/caprylic triglyceride is a combined tri-ester, a blend of capric and caprylic acids. It is also known as fractionated coconut oil.

Cetrimide=Cetrimide is an antiseptic which is a mixture of different quaternary ammonium salts including cetrimonium bromide. It was first discovered and developed by ICI and introduced under the brand name Cetavlon. It is used as a 1-3% solution for cleaning roadside accident wounds.

HEC=Hydroxyethyl cellulose, also known by the trade name NATROSOL®, is a gelling and thickening agent derived from cellulose. It is widely used in cosmetics, cleaning solutions, and other household products.

Glycerin=Glycerol is a simple polyol compound. It is a colorless, odorless, viscous liquid that is sweet-tasting and non-toxic. The glycerol backbone is found in all lipids known as triglycerides. It is widely used in the food industry as a sweetener and humectant and in pharmaceutical formulations. Glycerol has three hydroxyl groups that are responsible for its solubility in water and its hygroscopic nature.

Kara base=a hair conditioning agent or a "base conditioner". In this disclosure, it should be understood that Kara base is optional and can be left out of any formulation or replaced with any base conditioner or with any other generic formulation used as a hair conditioning agent. Base conditioner=any base conditioner commercially available which have ingredients of, for example, Aqua, Cetearyl Alcohol, Glycerin, Phenoxyethanol, Distearoylethyl Dimonium Chloride, Behentrimonium Chloride, Panthenol, Isopropyl Alcohol, Hydrolysed Sweet Almond Seedcake T-20=Tween 20 is oil-in-water emulsifier, can be used as solvent, diffusant, stabilizer, lubricant and anti-static agent etc.

TWEEN® 20=Polyethylene glycol sorbitan monolaurate, Polyoxyethylenesorbitan monolaurate PG=Propylene glycol (IUPAC name: propane-1,2-diol) is a synthetic organic compound with the chemical formula C3H8O2. It is a viscous, colorless liquid.

EDTA=Ethylene-diamine-tetra-acetic acid (EDTA) is a calcium chelating agent Sodium Benzoate=Sodium benzoate is a substance which has the chemical formula NaC7H5O2. It is a widely used food preservative, with an E number of E211.

Phenoxy=a preservative (a "procrastinator"), used in trace amounts.

Coconut Oil=Coconut oil, or copra oil, is an edible oil extracted from the kernel or meat of mature coconuts harvested from the coconut palm.

Argon Oil=Argan oil is a plant oil produced from the kernels of the argan tree (*Argania spinosa* L.)

Jojoba Oil=Jojoba is the liquid produced in the seed of the *Simmondsia chinensis* plant, Curry leaf Extract=the extract of the curry tree which is a tropical to sub-tropical tree in the family Rutaceae, which is native to India and Sri Lanka Beetroot Extract=extract of *Beta vulgaris* or related species DIASLEEK®-802=polyquaternium-73 is a cationic polymer preparation and is a silicone compound to prevent dryness in hair and scalp.

Karacyne=a keratin-derived protein

DC-245=Cytopentosyloxane, which is a Silicone fluoride substance used as a conditioning agent Soya Lecithin=an amphiphilic extract of soy Collagen=animal protein found in connective tissue G-700=a surfactant, foaming agent and sunscreen agent CPAB=cocamidopropyl betaine (an amphoteric surfactant)

Amaport=a herbal extract with properties that interact with or change physiological or chemical properties of another compound Vitamin A=Retinol. It normalizes skin's texture and smoothes out fine lines. The more stable form is Retinyl Palmitate.

Vitamin C=Ascorbic Acid. It is an antioxidant, skin lightening agent, pH adjuster, preservative and also rebuilds healthy collagen fibers. It is also used in the form of Ascorbyl Palmitate (a derivative of Vitamin C).

Vitamin E=Tocopherol. It is an antioxidant, prevents UV damage to skin and also moisturizes skin.

Panthenol=Vitamin B5. It is a humectant.

Alpha Hydroxy Acids. Commonly used ones are citric acid, glycolic acid and lactic acid. They aid in skin renewal by exfoliating the top layer of epidermis, improves skin's texture, aids in better penetration of active ingredients, restores moisture and reduces wrinkles. They find use in anti-aging products.

Salicylic Acid is a beta hydroxy acid. It is a debriding agent, helps in exfoliation of dry skin and reduces oiliness, acne and appearance of fine lines. It is mostly used in treating adult acne and chemical peels.

Humectants such as Glycerin are very commonly used humectant (ability to absorb moisture from air and entrap it into the skin). Hence, it hydrates and provides a skin barrier.

Hyaluronic Acid: It is a strong hydrating complex. It can hold up to 1000 times water in skin.

It is commonly used in anti-aging preparations for deep hydration.

Lecithin: It is a water attracting agent and hence hydrates and improves the texture of skin. It also allows the ease of spread onto the skin.

Silicones such as Dimethicone/Cyclomethicone are a group of silicone molecules. It gives cosmetic products a smooth texture without blocking pores, gives slip and glide to products. It is widely used in skin care, make up, hair care and hair styling preparations.

Sunscreen Agents such as Avobenzone, Mexoryl, Oxybenzone, Benzophenone are UV filters absorb or block UVA rays.

Titanium Dioxide is a physical UV blocker for both UVA and UVB.

Bleaching Agents such as Hydroquinone, Kojic Acid are skin whitening agents and skin bleaching agents.

Antioxidants include Resveratol and Butylated Hydroxy Toluene (BHT)

Preservative include Parabens, Benzoyl Peroxide

Soothing Agents such as Allantoin sooth and heal skin.

Aloe is extremely soothing and protective in nature. It is a natural oxygenator (draws and holds oxygen to skin) so is a very effective healing agent. It is also a natural astringent.

Camphor is a cooling agent and hence alleviates itching, irritation and redness.

Emollients such as Cetyl alcohol, Stearyl Alcohol, Ceteareth 20, Cetearyl Alcohol act as emollients (lubricants) and emulsifiers.

Isopropyl Isostearate, Isopropyl Palmitate, Isopropyl Myristate are emollients and hence form a film on skin and penetrates easily into the skin.

Castor Oil is a barrier agent and emollient.

Jojoba Oil is a moisturizer and a natural cellular renewal ingredient.

Avocado Oil: It is a skin conditioner and moisturizer that readily penetrates the skin.

Caprylic/Capric Triglyceride are barrier agents and emollients.

Glyceryl Oleate, Glyceryl Stearate, Glyceryl Cocoate, Glyceryl Stearate all act as emulsifiers.

Glyceryl Cocoate is a Surfactant (foaming and cleansing agent). Glyceryl Stearate SE also gives pearlizing effect in shampoos and opacifier in creams and lotions.

Beeswax is a barrier and emulsifying agent.

Candellila Wax is occlusive in nature and is used as a binder in lipsticks and creams.

Carnauba Wax is a barrier agent and texturizer.

Kaolin is an oil absorbing powder and gives color and slip. It is mostly used in face masques for oily/combination skin.

Caffeine: Alleviates puffiness under eyes.

Lanolin alcohol is used as a thickener for shampoos and bath gels. It gives cosmetics a creamy texture and high gloss. Lanolin oil is basically dewaxed lanolin and acts as a skin moisturiser and reduces stickiness of creams and lotions. It is found in hair conditioners, fingernail conditioners and skin cosmetics.

The invention claimed is:

1. A cosmetic skin-care formulation designed to reduce skin wrinkles, specifically excluding cocamidopropyl betaine and sodium lauryl ether sulfate, and comprising the following amounts of components measured as weight-percent:
   Lunasin at 5%
   argan Oil from 0.1% to 5%, make
   a rheology modifier from 0.3% to 1.4%,
   sodium benzoate from 0.2% to 0.3% or Imidazolidinyl urea from 0.3%-0.4%,
   potassium sorbate from 0.1% to 0.4%,
   EDTA from 0.1% to 0.2%,
   niacinamide from 0.01% to 1%,
   allantoin from 0.1% to 0.4%,
   glycerine from 0.5% to 2%,
   polyquaternium-10 from 0.1% to 0.4%
   and water to 100%.

2. The cosmetic skin-care formulation of claim 1 additionally comprising sodium lactate from 0.5% to 2%, Aloe Vera extract from 0.1% to 0.6% and cetrimide from 0.1% to 0.6%.

3. The cosmetic skin-care formulation of claim 1 additionally comprising alkyl polyglucoside as a surfactant.

4. The cosmetic skin-care formulation of claim 1 additionally comprising: coloring agents, and fragrances agents.

5. The cosmetic skin-care formulation of claim 1 additionally comprising pearlising agents, preservatives, perfumes and colorants.

6. The cosmetic skin-care formulation of claim 1 additionally comprising: a glycyl-L-histidyl-L-lysine copper complex designed to have a firming effect on skin.

7. The cosmetic skin-care formulation of claim 1 additionally comprising: Palmitoyl Pentapeptide designed to increase collagen synthesis.

8. The cosmetic skin-care formulation of claim 1 additionally comprising: Pentapeptide 3, designed to relax muscles in the skin.

9. The cosmetic skin-care formulation of claim 1 additionally comprising: rice & soy peptides.

10. The cosmetic skin-care formulation of claim 1 additionally comprising beeswax.

11. The cosmetic skin-care formulation of claim 1 further comprising a telomerase activator at a concentration of 10-50 mg/ml.

12. The cosmetic skin-care formulation of claim 1 further comprising both gold nanotubes at a concentration of less than 0.0001 wt % and telomerase activator at a concentration of 10-50 mg/ml.

* * * * *